United States Patent
Perry et al.

(10) Patent No.: US 6,368,817 B1
(45) Date of Patent: Apr. 9, 2002

(54) IDENTIFICATION OF SALMONELLA

(75) Inventors: John David Perry; Michael Ford, both of Newcastle-Upon-Tyne (GB)

(73) Assignee: Newcastle Upon Tyne Hospitals National Health service Trust (GB)

(*) Notice: Subject to any disclaimer, the term of this patent is extended or adjusted under 35 U.S.C. 154(b) by 0 days.

(21) Appl. No.: 09/355,066

(22) PCT Filed: Jun. 4, 1998

(86) PCT No.: PCT/GB98/01645

§ 371 Date: Jul. 8, 1999

§ 102(e) Date: Jul. 8, 1989

(87) PCT Pub. No.: WO98/55644

PCT Pub. Date: Dec. 10, 1998

(51) Int. Cl.$^7$ ............................................... C12Q 1/02
(52) U.S. Cl. ........................................ 435/29; 435/34
(58) Field of Search ....................... 435/7.9, 18, 24, 435/29, 34, 38, 39, 40; 540/221

(56) References Cited

U.S. PATENT DOCUMENTS

| | | | |
|---|---|---|---|
| 3,856,628 A | 12/1974 | Sbarra | 195/103.5 R |
| 4,591,554 A | 5/1986 | Koumura et al. | 435/18 |
| 5,098,832 A | 3/1992 | Rambach | 435/34 |
| 5,194,374 A | 3/1993 | Rambach | 435/34 |
| 5,210,022 A | 5/1993 | Roth et al. | 435/34 |
| 5,464,755 A * | 11/1995 | Bochner | 435/34 |
| 5,726,031 A * | 3/1998 | Roth et al. | 435/34 |
| 6,008,008 A * | 12/1999 | James et al. | 435/34 |
| 6,136,554 A * | 10/2000 | Bochner | 435/34 |

FOREIGN PATENT DOCUMENTS

| | | |
|---|---|---|
| EP | 0025467 | 5/1983 |
| EP | 0214340 | 3/1987 |
| EP | 0282733 | 9/1988 |
| EP | 0614896 | 9/1994 |
| EP | 0711359 | 5/1997 |
| GB | 2050418 | 1/1981 |
| WO | 92/12259 | 7/1992 |
| WO | 94/09152 | 4/1994 |
| WO | 94/28163 | 12/1994 |
| WO | 95/04156 | 2/1995 |
| WO | 95/04157 | 2/1995 |
| WO | 96/30543 | 10/1996 |
| WO | 97/41138 | 11/1997 |

OTHER PUBLICATIONS

James A. L. Evaluation of Cyclohexenoesculetin–beta–D –Galactoside and 8–Hydroxyquinoline–beta–D–Galactoside as Substrates for the Detection of Beta–Galactosidase. Applied and Environmental Microbiology 62(10)3868–3870, Oct. 1996.*

James A. L. Cyclohexenoesculetin–beta–D–Glucoside: A New Substrate for the Detection of Bacterial beta–D–Glucosidase. J of Appllied Micro 82(4)532–536, Apr. 1997.*

I. Ketyi, "Feeding By Mucin and Intestinal Growth of Some Enteric Bacterial Pathogens", *Acta Microbiologica Hungarica,* vol. 35, No. 4, 1988, pp. 389–395.

P. Chevalier, et al., "X–α–Gal–Based Medium for Simultaneous Enumeration of Bifidobacteria and Lactic Acid Bacteria in Milk", *Journal of Microbiological Methods,* vol. 13, 1991, pp. 75–83.

A.L. James, et al., "Cyclohexenoesculetin–β–D–Glucoside: A New Substrate for the Detection of Bacterial β–D–Glucosidase", *Journal of Applied Microbiology,* vol. 82, 1997, pp. 532–536.

H. Kodaka, et al., "Evaulation of New Medium with Chromogenic Substrates for Members of the Family *Enterobacteriaceae* in Urine Samples", *Journal of Clinical Microbiology,* vol. 33, No. 1, Jan. 1995, pp. 199–201.

M. Manafi, et al., "Fluorogenic and Chromogenic Substrates used in Bacterial Diagnostics", *Microbiological Reviews,* vol. 55, No. 3, Sep. 1991, pp. 335–348.

A. Rambach, "New Plate Medium for Facilitated Differentiation of *Salmonella spp.* from *Proteus spp.* and Other Enteric Bacteria", *Applied and Environmental Microbiology,* vol. 56, No. 1, Jan. 1990, pp. 301–303.

H. Dusch, et al., "Evaluation of Five New Plating Media for Isolation of Salmonella Species", *Journal of Clinical Microbiology,* vol. 33, No. 4, Apr. 1995, pp. 802–804.

A.L. James, et al., "Evaluation of Cyclohexenoesculetin–β–D–Galactoside and 8–Hydroxyquinoline–62 –D–Galactoside as Substrates for the Detection of β–Galactosidase", *Applied and Environmental Microbiology,* vol. 62, No. 10, Oct. 1996, pp. 3868–3870.

* cited by examiner

*Primary Examiner*—Ralph Gitomer
(74) *Attorney, Agent, or Firm*—Ostrolenk, Faber, Gerb & Soffen, LLP

(57) ABSTRACT

A new culture medium for identifying the presence of Salmonella inenterobacteria samples, especially faeces, contains two chromogenic enzyme substrates, one of which is a substrate for α-D-galactosidase, for which Salmonella is positive. The other substrate is one for which Salmonella is negative such as β-D-galactosidase. The substrates are incorporated into an agar medium. Positive and negative results are found to be readily observable where one of the substrates is an esculetin, preferably a cyclohexenoesculetin compound in the presence of ferric ions, which produces a black color, and the other substrate is an indoxyl compound, for instance, a 5-bromo-4-chloro-3-indolyl compound which produces a green colored enzymic reaction product.

57 Claims, No Drawings

IDENTIFICATION OF SALMONELLA

This application claims benefit under rule 371 of PCT GB-98/01645 filed Jun. 4, 1998 which claims benefit from EP 97/3846.6 filed Jun. 4, 1997.

The present invention relates to processes for identifying the presence of Salmonella species in a sample, as well as culture media suitable for such identification processes.

Members of the genus Salmonella constitute the most important causes of food poisoning in the UK. At present, the only effective means of diagnosis involves cultural isolation of the causative organism from faeces. This however is not straightforward as specialised media and reagents are required to isolate relatively small numbers of Salmonellae from a massive amount of commensal flora in the guts. Selective media have been developed for this purpose which rely on the visualisation of simple biochemical features such as production of hydrogen sulphide or non-fermentation of lactose.

A useful review of five plating media for isolation of Salmonella species and a comparison against Hektoen enteric agar, a standard medium, is described by Dusch et al in J. Clin. Microbial. (1995) 33(4), 802 to 804. All but one of the media are solid (standard agar concentration) whilst one is a semi solid reduced agar concentration medium. For the solid media, the compounds which are produced in the presence of microbial growth are selected so as to be visible to the naked eye. In order that the visualised compounds are associated with microbial colonies, those compounds must be non-diffusible in the culture medium. These media typically test for two different biochemical characteristics of bacterial colonies and the results are such that positive and negative results of each of the two tests can be observed with positive or negative results of the other test. Some of the biochemical tests observe the activity of specific enzymes by the use of chromogenic substrates which are uncoloured or non-fluorescent but which generate enzymic reaction products which are coloured or fluorescent and can hence be observed in the presence of the substrates. Sometimes the enzymic reaction product may react with a further component of the culture medium to generate the visible product, for instance metal ions or pH indicators, where the reaction product is an acid or base.

It is known to include in the culture medium substrates for two different enzymes which have different enzymic reaction products, each of which can be observed in the presence of the other (and of each of the substrates themselves).

One enzyme substrate which is commonly used in the identification of Salmonella is a substrate for β-galactosidase. Salmonella is generally negative for this enzyme activity, but most other members of the Enterobacteriaceae are positive. One β-galactosidase substrate whose enzymic reaction product is non-diffusible is 5-bromo-4-chloro-3-indolyl-β-D-galactopyranoside (X Gal). Other indoxyl and halogenated indoxyl compounds are useful as substrates and have reaction products which are visible and non-diffusible in agar culture media.

X-Gal is used as a substrate in Rambach medium, described inter alia in U.S. Pat. No. 5,194,374. It is used in combination with an alkanediol, which is metabolised by Salmonella to form an acid reaction product which is visualised by the incorporation of a pH indicator such as neutral red.

In EP-A-0516817, a culture medium for detecting Salmonella comprises a chromogenic β-galactosidase substrate and, in addition, glucuronate and a pH indicator. This mixed medium is alleged to be more selective than Rambach medium since almost all Salmonella species tested, but few other bacterial species ferment glucuronic acid resulting in a lowering of the pH.

In WO-A-94/0 1952, a 5-bromo-4-chloro-3-indolyl compound which is a substrate for an esterase enzyme is used to identify Salmonellae, which are positive for such enzymes. The substrate is an ester of a $C_{7-10}$-fatty acid. It is suggested that the medium may be supplemented to eliminate non-Salmonella bacteria, such as using properties relating to cleavage or metabolism of β-galactosides and β-glucosides (for both of which Salmonella is negative).

Rambach medium and the X-gal glucuronic acid combination were found by Dusch et al to have less than optimal sensitivities. A further medium comprising xylose, lysine and Tergitol 4 has very good sensitivity and specificity. The culture medium includes the surfactant Tergitol 4 to inhibit Proteus, and determining hydrogen sulphide formation from sodium thiosulphate in the medium which is visualised by the incorporation of ferric ions.

It is known that Salmonella species produce α-galactosidase, but it is likely that that enzyme would be considered a poor marker for Salmonella since it is produced by many related genera, such as Escherichia, Citrobacter, Klebsiella, Enterobacter and Shigella.

In Acta Microbiol Hung. (1988) 35(4), 389–395 Ketyi, I. discusses the α-galactosidase activity of various species of entero-bacteria including Salmonella, Shigella and *E-coli*. He indicated that enzymic activity is a general feature of Enterobacteriaceae. He used melibiose, as an indicator of α-galactosidase positive strains. Melibiose is not a chromogenic compound.

In WO-A-9630543 a chromogenic β-galactosidase substrate is used in combination with a mixture of sugars including mannitol, with xylose and melibiose for identifying Salmonella. The sugars are cleaved to form acids and the growth medium contains a pH indicator. However the acids which change the pH are products of a series of enzymic reactions on the product of sugar metabolism.

James et, al in App. Env. Microbiol. (1996), 62(10) 3868–170 and in J. App. Microbiol.(1997),82, 532–536, describe a new β-galactosidase substrate for use in place of X-Gal. The substrate is a derivative of cyclohexenoesculetin, of which the aglycone released by hydrolysis by β-galactosidase forms a black-brown complex with ferric ions in the medium. The new substrate, CHE-Gal, gave good correlation with X-Gal, that is high specificity and high sensitivity for detecting β-galactosidase activity.

These cyclohexenoesculetin substrates and other esculetin derivatives are described further and claimed in WO-A-9741138 (not published at the priority date of the present invention).

One aspect of the present invention is based on the need for culture media which are very sensitive to Salmonella whilst being highly specific, thereby minimising subsequent confirmatory tests. These types of test often need to be carried out with the inadequately specific media of the prior art. A second aspect of the invention is based on the provision of a medium comprising two chromogenic substrates which gives readily observable results. A visual determination can be easily made of the presence and absence of enzymic reaction products of each substrate regardless of the presence or absence of the enzymic reaction product of the other substrate.

According to a first aspect of the present invention there is provided a new process in which the following steps are carried out:

1. a sample suspected of containing Salmonella bacteria is cultured in the presence of a nutrient,
2. the bacterial culture is contacted with each of two enzyme substrates,
3. the presence of the enzymic reaction products of each of the substrates is accessed after step 2 to determine whether or not growth of Salmonella species has taken place, in which the first substrate is a substrate for an enzyme for which Salmonella is negative, the process being characterised in that the second substrate is a substrate for α-galactosidase and in that both substrates are chromogenic.

The present inventors believe that it is the first time that α-galactosidase has been used as a marker for Salmonella using an α-galactosidase specific chromogenic substrate, that is a substrate for which the enzymic product of the reaction in the presence of α-galactosidase is chromogenic without being subjected to further enzymic reactions. Thus, the inventors have recognised the utility of combining β-galactosidase and α-galactosidase as markers for detecting Salmonella species. The method is useful for carrying out the usual tests to identify Salmonella. It is not necessary for there to be any specific expectation of Salmonella presence in a clinical sample tested in the present invention. Thus the invention is suitable for screening to exclude Salmonella (giving a negative result) as well as for positive tests.

The enzyme for cleaving the said first substrate, the activity for which Salmonella is negative, is selected such that a positive result (cleavage) can exclude a large number of Enterobacteriaceae. Salmonellae are negative for β-glucosidase and a substrate for β-glucosidase could therefore be used. Many other enterobacteria are also negative for β-glucosidase. Best results are achieved where substrates for that enzyme are used in combination further with other enzyme substrate. Such other substrates would be selected to help distinguish Salmonella from such other β-glucosidase negative species. Most conveniently the first substrate is selected to be cleavable by β-galactosidase. The substrate therefore should preferably be a derivative of β-D-galactopyranoside.

Although the invention may be used in a panel of biochemical tests, each of which is carried out in an individual container, on a single bacterial colony, it is preferred that the process is used for samples containing a mixture of bacterial species which are cultured together on a body of culture medium in a single container. The culture medium is preferably a solid (gelled) medium, most conveniently based on agar. Other conventional support materials for bacterial culturing can be used.

The sample, as mentioned above, preferably contains a mixture of bacterial species. It may be a direct sample, inoculated using a suitable technique onto the culture medium. Thus it may be a sample of food, water, or bodily fluid of a patient, usually blood, urine or, most preferably faeces. Alternatively a direct sample may, prior to carrying out the process, be enriched by inoculating the direct sample into an enrichment broth and culturing the broth for a period of time, for instance 24 hours, before inoculating a portion of the bacterial culture onto the culture medium for the process of the invention. The enrichment medium is selected so as to favour the growth of Salmonella species over other common enterobacteria such as *E.coli* and Proteus. Suitable enrichment media are, for instance, tetrathionate or selenite broths.

The medium in which the first culturing step of the invention is carried out preferably includes components which favour growth of Salmonella. Thus the medium may contain known inhibitors of other enterobacterial growth such as brilliant green, bile salts or desoxycholate sodium salt.

Where the enzyme activity for which Salmonella is negative is β-galactosidase, the first step of the process of the present invention is preferably carried out in the presence of a β-galactosidase promoter of known type, for instance lactose or, preferably, isopropyl-β-D-thiogalactopyranoside.

In the process the enzyme substrates are each chromogenic. In this specification, the term chromogenic encompasses fluorogenic. The enzymic reaction products or each substrate are preferably directly visible, for instance as coloured compounds, optionally in the presence of other components such as metal ions, preferably by the naked eye in visible light. Alternatively the reaction products may be detectable spectrophotometrically, by observing absorbed radiation of any predetermined wavelength, or fluorometrically by observing fluorescence.

Alternatively the direct enzyme reaction products may be visible after further chemical, non-enzymic reaction.

It is preferred that the direct product of the enzymic cleavage is detectable without further chemical reaction, since such further reactions may be non-specific and cause false readings. The invention does not include the use of pH indicators to identity the presence of the cleavage product.

Where both substrates are in physical admixture in the same body of culture medium, the enzymic reaction products of the two substrates must be different compounds, at least one of which should be detectable in the presence of the other and in the presence of both the substrates themselves. The other reaction product might be masked by the first, or be visible in its presence. Thus any combination of positive and negative reaction can be observed in the reaction medium.

Although the step of contacting the substrates with the cultured bacteria may take place after culturing has been carried out for a period of time, and in a step in which no further bacterial growth or metabolism takes place, preferably culturing takes place in the presence of the enzyme substrates. Thus the substrates are incorporated into the culture medium at the beginning of the culturing step 1 of the process. The substrates should, consequently, be non-toxic for bacteria, or at least for Salmonella, allowing growth of, especially, Salmonella, to take place.

The present inventors have discovered that a particularly useful combination of enzymic substrates comprises a substrate which generates an enzymic reaction product which is an indoxyl compound, including a halogen substituted compound, and a second substrate which is an esculetin, especially a 3,4-cyclohexenoesculetin compound. Where the latter substrate is used, during or after contacting of the cultured bacteria with the substrate ferric ions should be contacted with the medium. This leads to generation of a brown black colour with the enzymic reaction product of such a substrate.

According to a second aspect of the invention there is provided a process in which a bacterial sample is cultured on a solid medium which comprises, in admixture, two chromogenic enzyme substrates, the enzymic reaction products of which are substantially non-diffusible in the solid medium, are capable of being detected optically in the presence of the respective substrates, and are different compounds, in which one of the substrates is an indoxyl compound and characterised in that the other of the substrates is an esculetin compound, preferably a 3,4-cyclohexenoesculetin compound.

Preferably one of the enzyme substrates is a substrate for a glycosidase, for instance β-galactosidase, α-galactosidase or β-glucosidase. Preferably one of the substrates is a substrate for a different glycosidase enzyme, although may alternatively be an esterase substrate. Preferably both substrates are for different glycosidase enzymes. Most preferably one substrate is for α-galactosidase and the other is a substrate for β-galactosidase.

The esculetin substrate is substituted at the 6- or, preferably, 7-hydroxyl by a glycoside. Substituted 3,4-cyclohexenoesculetin compounds which produce non-diffusible complexes with metal ions, for instance, ferric ions, may also be used. Thus the cyclohexene ring may be substituted, or the coumarin ring system may be substituted, by one or more substituents.

The esculetin compound suitably has the general formula

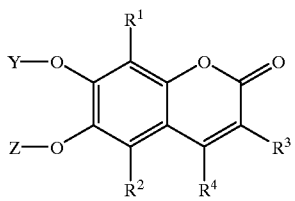

(I)

wherein
    each of $R^1$ and $R^2$ independently represents a hydrogen or a halogen atom or another group which does not interfere with subsequent iron chelation;
    each of $R^3$ and $R^4$ independently represents a hydrogen atom or a $(C_1-C_8)$ alkyl or $(C_6-C_{10})$ aryl $(C_1-C_8)$ alkyl or an optionally modified carboxyl-bearing group of the general formula —$CH_2(CH_2)_n COX$, where n is a number from 0 to 3 and X represents a hydroxyl group or another hydrophilic group,
    and, $R^3$ may alternatively represent an acyl group of the general formula —COR, in which R represent a $(C_1-C_8)$alkyl, $(C_6$ or $C_{10})$aryl$(C_1-C_8)$alkyl or $(C_5-C_8)$ cycloalkyl group,
    provided that $R^3$ and $R^4$ between them contain at least three carbon atoms;
    or $R^3$ and $R^4$ together with the carbon atoms to which they are attached form a $(C_5-C_8)$ cycloalkene ring; and
    one of Y and Z represents the enzymatically cleavable group and the other of Y and Z represents a hydrogen atom;
    or a suitable salt or hydrate thereof.

Hereafter in this specification the term "compound" includes "salt" or "hydrate" unless the context requires otherwise.

As used herein the term "halogen" or its abbreviation "halo" means fluoro, chloro, bromo and iodo.

The expression "atom or group which does not interfere with iron chelation" refers to the fact that one of the principle means of detection of aglycones of general formula I is by chelation by means of hydroxyl groups at the 6 and 7 positions of the coumarin ring system. Groups which do not interfere with this chelation may be substituted at $R^1$ and/or $R^2$. Examples include hydrogen, hydroxyl, halogen or $(C_1-C_6)$ alkyl. The halogen atom may be a fluorine atom or a chlorine atom and the lower alkyl group may be methyl, ethyl, propyl, butyl or benzyl.

As used herein the term "$(C_1-C_8)$alkyl" refers to straight chain or branched chain hydrocarbon groups having from one to eight carbon atoms. Illustrative of such alkyl groups are methyl, ethyl, propyl, isopropyl, butyl, isobutyl, sec-butyl, tert-butyl, pentyl, neopentyl, hexyl, heptyl and octyl. From one to four carbon atoms may be preferred.

As used herein the term "$(C_1-C_{10})$alkyl" refers to straight chain or branched chain hydrocarbon groups having from one to ten carbon atoms. Illustrative of such alkyl groups are methyl, ethyl, propyl, isopropyl, butyl, isobutyl, sec-butyl, tert-butyl, pentyl, neopentyl, hexyl, heptyl, octyl, nonyl and decyl. From one to six carbon atoms may be preferred.

The term "$(C_6$ or $C_{10})$aryl" includes phenyl and naphthyl.

As used herein, the term "$(C_5-C_8)$ cycloalkene ring" refers to an alicyclic ring having from 5 to 8 atoms and having in addition one or more double bonds. Illustrative of such cycloalkenyl groups are cyclopentenyl, cyclohexenyl, cycloheptenyl and cyclooctenyl.

In compounds of this invention, the presence of an asymmetric carbon atom gives rise to enantiomers. The presence of several asymmetric carbon atoms give rise to diastereoisomers, each of which consists of two enantiomers, with the appropriate R or S steriochemistry at each chiral centre. The invention is understood to include all such diastereoisomers, optically active enantiomers and mixtures thereof.

The term "suitable salt" refers to a salt prepared by contacting a compound of formula I with an acid or base whose counterpart ion does not interfere with the intended use of the compound. Examples include the sodium salt or magnesium salt of a phosphate derivative or the salt formed from a primary, secondary or tertiary amine where the compound or general formula I is a carboxylic acid. An example of a primary amine salt can be the cyclohexylammonium salt, a suitable secondary amine salt may be the piperidine salt and a tertiary amine salt may be the triethylamine salt.

Preferred compounds of general formula I include those in which, independently or in any compatible combination:
    $R_1$ is chlorine or, preferably, hydrogen;
    $R^2$ is chlorine or, preferably, hydrogen;
    $R^3$ is $(C_1-C_4)$alkyl, particularly butyl, or benzyl;
    $R^4$ is $(C_1-C_4)$alkyl; or, —$CH_2(CH_2)_n COX$, where n is a number from 0 to 3 and X represents a hydroxyl group or one of the following hydrophillic groups, namely:
    —$NHCH_2CONHCH_2CO_2H$
    —$NHCH_2CONHCH_2CONHCH_2CO_2H$
    —$NHCHCH_2CONH_2$

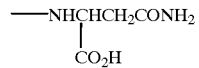

$R^3$ and $R^4$ together with the carbon atoms to which they are attached form a $(C_5-C_8)$cycloalkene ring, preferably a cyclopentenyl or cyclohexenyl ring;
where $R^3$ is —$CH_2(CH_2)_n COX$, where n is a number from 0 to 3, then the group X is as previously defined,
the enzymatically cleavable group represented by Y or Z is an α- or, preferably, β-linked sugar residue such as β-D-glucose, β-D-galactose, β-D-xylose, β-D- glycuronic acid or N-acetyl-β-D-glucosamine. Sugar residues derived from galactose, especially β-D-galaclopy-anosides, are most preferred compounds.

Compounds in which $R^3$ and $R^4$ together with the carbon atoms to which they are attached form a cyclopentene or a cyclohexene ring are especially preferred.

A preferred compound of general formula (I) is: 3,4-cyclohexenoesculetin-β-D-galactoside,

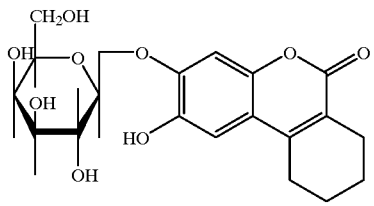

The enzymic reaction product of a 3,4-cyclohexenoesculetin substrate produces a brown black complex in the presence of ferric ion. The enzymic reaction product of a 5-bromo-4-chloro-3-indolyl compound produces a green or blue colour in the presence of oxygen. Other indoxyl derivatives are available, which have different substituents so as to generate a different coloured reaction product, for instance which is magenta, rose, blue, salmon red, and any of these can be used in place of the 5-bromo-4-chloro-3-indolyl compound. A bacterial colony which is positive for the enzyme which cleaves the esculetin substrate generates a black colour in the presence of ferric ions. Colonies which are positive for the enzyme which cleaves the 5-bromo-4-chloro-3-indolyl substrate produce a green colour. Colonies which are positive for both enzymes can be distinguished from colonies which are positive for the enzyme of which the indolyl compound is a substrate but which are negative for the other enzyme or negative for both. The reaction product of the esculetin substrate masks the reaction product of the indoxyl substrate, however, so that colonies which are positive for both enzymes cannot necessarily be distinguished from those which are positive only for the enzyme of which the esculetin compound is a substrate.

The esculetin substrate is generally present in a concentration of about 200 to 500 mg/l in the agar medium, more preferably about 300 mg/l. The indoxyl substrate is present in amounts of up to 300 mg/l, although it is generally unnecessary to use concentrations higher than 100 mg/l. The amount is usually at least 35 mg/l, for instance about 70 mg/l. This concentration of ferric ions is usually about 400 to 1000 mg/l (based on ferric ammonium citrate) for instance about 500 mg/l.

Preferably the method of the second aspect of the present invention is for identifying the presence of Salmonella. The culturing of the bacteria is therefore preferably carried out in the presence of an inhibitor of other enterobacteria and/or a promoter for β-galactosidase.

According to a further aspect of the invention there is provided a new composition for use in the culturing of bacteria which comprises in admixture a first chromogenic enzyme substrate for β-galactosidase and a second chromogenic enzyme substrate, the substrates being selected such that the enzymic reaction products of the two enzymes are different compounds and is characterised in that the second substrate is a substrate for α-galactosidase.

The new composition of this aspect of the invention is suitable for use in the process of the first aspect of the invention. Preferably the composition contains other components suitable for carrying out the culturing step of the bacteria, and thus contains one or more nutrients for bacterial growth, and preferably a support substance, for instance a gelling substance such as agar. Preferably the composition is in a dry, hydratable form whereby it can be hydrated to form a ready-to-use culture medium. The medium preferably contains the other components useful in the culture medium as described above in connection with the process.

According to a further aspect of the invention there is provided a new composition for use in the culturing of bacteria comprising in admixture a first chromogenic enzyme substrate which is an indoxyl compound and a second chromogenic enzyme substrate, and is characterised in that the second enzyme substrate is an esculetin, preferably a 3,4-cyclohexenoesculetin, compound.

In this aspect of the invention, the composition also preferably contains one or more nutrients for bacterial growth as well as a support substance, for instance a gelling substance such as agar. The composition is preferably in hydratable form and should contain further ferric salt, which generates the black compound in the presence of the enzymic reaction product of the esculetin compound. Ferric ammonium citrate is conveniently used although ferric gluconate or other salts could be used as alternative sources of ferric ions.

The compositions may be based on selective basal media which inhibit normal microbial flora and allow selective growth of Salmonella. Known media of this type are bismuth sulphite agar, Brilliant green agar, Hektoen enteric agar and Salmonella/Shigella agar.

Other preferred embodiments of this further aspect of the invention are described above in connection with the novel processes. As mentioned above, it is believed that this is the first time that α-galactosidase has been used as a marker for Salmonella in the detection of Salmonella in a mixed sample.

Accordingly in a further aspect of the invention there is provided a new use of a chromogenic α-D-galactoside enzyme substrate to detect the presence of Salmonella species in a mixed species sample. Preferably the detection is carried out by culturing the mixed sample on an agar medium. Chromogenic α-galactosidase substrates are commercially available. The enzyme substrate is preferably 5-bromo-4-chloro-3-indolyl-α-D-galactopyranoside.

The invention is described further in the following example:

EXAMPLE

The following base culture medium is made up. It encourages the growth of Salmonella at the expense of other enterobacteria by incorporation of desoxycholate.

| DCA Hynes Base (per liter) | |
| --- | --- |
| Beef extract | 5.0 g |
| Balanced peptone No. 1 | 5.0 g |
| Sodium citrate | 8.5 g |
| Sodium desoxycholate | 5.0 g |
| Agar No. 2 | 12.0 g |
| Chromogenic Mix (per liter) | |
| 5-Bromo-4-chloro-3-indolyl-α-D-galactopyranoside | 70 mg |
| 3,4-cyclohexenoesculetin-β-D-galactopyranoside | 300 mg |
| Ferric ammonium citrate | 500 mg |
| Isopropyl-β-D-thiogalactopyranoside | 30 mg |

All of the above ingredients are dissolved in 1 liter of distilled water and autoclaved at 116° C. for 10 minutes. The agar is then poured in sterile plastic petri dishes and allowed to set.

Evaluation

Members of the Enterobacteriaceae of known identity were obtained in pure culture and inoculated onto the new selective medium. All plates were incubated at 37° C. for 18 hours and examined for colour production. 1020 of these strains were known to be Salmonella and had been consecutively isolated from faeces samples at both the Freeman Hospital (120 strains) and the Newcastle Regional Public Health Laboratory (900 strains). Of the 1020 Salmonella strains, 1016 (99.6%) produced a green colony characteristic of Salmonella. Of the remaining four strains there were three strains which did not produce α-galactosidase and remained colourless. These were two strains of Salmonella saint-paul and one strain of *Salmonella branderup*. The remaining strain was a β-galactosidase producing *Salmonella arizonae* which consequently produced a black colony.

Of the 300 non-Salmonella, only one strain produced a green colony typical of Salmonella. This was a highly atypical strain of *Escherichia coli* which did not produce β-galactosidase. 39 other strains of *E.coli* produced a typical black colony.

From the above results it can be seen that the culture medium including the substrates for α-galactoside and β-galactoside is extremely sensitive (99.6%) but still highly specific (99.9%) for the detection of Salmonella. Furthermore the results are easy to read.

What is claimed is:

1. A process of analyzing a sample suspected of containing Salmonella bacteria to determine whether such bacteria are present in which the following steps are carried out:
   a. culturing the sample in the presence of a nutrient to form a bacterial culture,
   b. contacting the bacterial culture with a first and a second enzyme substrate,
   c. assessing the bacterial culture after step b for the presence of the enzymic reaction products of each of said substrates, and
   d. determining from the assessment of step c whether or not growth of Salmonella species has taken place,
   wherein said first substrate is a substrate for an enzyme for which Salmonella is negative, said second substrate is a substrate for α-galactosidase, and both first and second substrates are chromogenic.

2. A process according to claim 1 in which either the first or the second substrate is an indoxyl compound.

3. A process according to claim 2 in which the indoxyl compound is a 5-bromo-4-chloro-3-indolyl compound.

4. A process according to claim 1 in which either the first or the second enzyme substrate is a esculetin compound.

5. A process according to claim 4 in which the esculetin compound is a 3,4-cyclohexenoesculetin compound.

6. A process according to claim 5 in which the esculetin compound has the general formula I (I)

wherein
  each of $R^1$ and $R^2$ is independently selected from the group consisting of hydrogen, halogen atoms hydroxyl, $(C_{1-6})$alkyl and benzyl groups;

$R^3$ is selected from the group consisting of acyl groups of the general formula —COR, in which R is selected from the group consisting of $(C_1-C_8)$ alkyl, $(C_6$ and $C_{10})$aryl $(C_1-C_8)$ alkyl and $(C_5-C_8)$ cycloalkyl groups,
  $R^4$ is selected from the group consisting of hydrogen atoms, $(C_1-C_8)$ alkyl, $(C_6$ and $C_{10})$ aryl $(C_1-C_8)$ alkyl groups, optionally modified carboxyl-bearing group of the general formula —$CH_2(CH_2)_n COX$, where n is a number from 0 to 3 and X represents a hydroxyl group or another hydrophilic group
  provided that $R^3$ and $R^4$ between them contain at least three carbon atoms;
  or $R^3$ and $R^4$ together with the carbon atoms to which they are attached form a $(C_5-C_8)$ cycloalkene ring; and
  one of Y and Z represents an enzymatically cleavable group and the other of Y and Z represents a hydrogen atom;
  or a suitable salt or hydrate thereof.

7. A process according to claim 6 in which $R^3$ and $R^4$, together with the carbon atoms to which they are attached, form a $C_{5-8}$-cycloalkene ring.

8. A process according to claim 7 in which $R^3$ and $R^4$, together with the carbon atoms to which they are attached, form a cyclohexene ring.

9. A process according to claim 1 in which one of the enzyme substrates is 5-bromo-4-chloro-3-indolyl-α-D-galactopyranoside.

10. A process according to claim 1 in which one of the enzyme substrates is 3,4-cyclohexenoesculetin-β-D-galactopyranoside.

11. A process according to claim 1 in which the sample which is cultured contains enterobacteria.

12. A process according to claim 11 in which the sample which is cultured is derived from an enrichment process in which a direct sample is cultured in an enrichment broth.

13. A process according to claim 11 in which the sample which is cultured in the process is a direct non-enriched sample.

14. A process according to claim 11 in which the direct sample is of faeces.

15. A process according to claim 1 in which the sample is cultured in the presence of an inhibitor of enterobacteria other than Salmonella.

16. A process according to claim 1 in which the sample is cultured on a solid medium.

17. A process according to claim 16 in which the culture medium on which culturing takes place contains said first and second enzyme substrates, the enzyme substrates being selected such that the enzymic reaction product of each of them is a different compound and is substantially non-diffusible in the culture medium.

18. A process according to claim 17 in which one of the substrates is an indoxyl compound and the other is an esculetin compound.

19. A process according to claim 18 in which the indoxyl compound is a 5-bromo-4-chloro-3-indolyl compound.

20. A process for culturing and detecting bacteria in a sample in which the bacterial sample is cultured on a solid medium which comprises, in admixture, two enzyme substrates, the enzymic reaction products of each of which are substantially non-diffusible in the solid medium, which are detected optically in the presence of the respective substrates, and are different compounds, wherein one of the substrates is an indoxyl compound and the other of the substrates is an esculetin compound.

21. A process according to claim 20 in which the esculetin compound is a 3,4-cyclohexenoesculetin.

22. A process according to claim 20 in which the esculetin compound has the general formula I

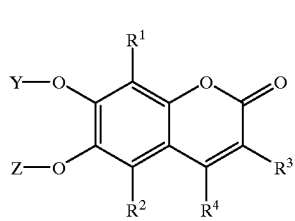

(I)

wherein
each of $R^1$ and $R^2$ is independently selected from the group consisting of hydrogen, halogen atoms hydroxyl, $(C_{1-6})$alkyl and benzyl groups;
$R^3$ is selected from the group consisting of acyl groups of the general formula —COR, in which R is selected from the group consisting of $(C_1-C_8)$ alkyl, $(C_6$ and $C_{10})$aryl $(C_1-C_8)$ alkyl and $(C_5-C_8)$ cycloalkyl groups,
$R^4$ is selected from the group consisting of hydrogen atoms, $(C_1-C_8)$ alkyl, $(C_6$ and $C_{10})$ aryl $(C_1-C_8)$ alkyl groups, optionally modified carboxyl-bearing group of the general formula —$CH_2(CH_2)_n COX$, where n is a number from 0 to 3 and X represents a hydroxyl group or another hydrophilic group
provided that $R^3$ and $R^4$ between them contain at least three carbon atoms;
or $R^3$ and $R^4$ together with the carbon atoms to which they are attached form a $(C_5-C_8)$ cycloalkene ring; and
one of Y and Z represents an enzymatically cleavable group and the other of Y and Z represents a hydrogen atom;
or a suitable salt or hydrate thereof.

23. A process according to claim 22 in which $R^3$ and $R^4$, together with the carbon atoms to which they are attached form a $C_{5-8}$ cycloalkene ring.

24. A process according to claim 23 in which $R^3$ and $R^4$, together with the carbon atoms to which they are attached, form a cyclohexene ring.

25. A process according to claim 20 in which the indoxyl compound is 5-bromo-4-chloro-3-indolyl-α-D-galactopyranoside.

26. A process according to claim 25 in which the esculetin compound is 3,4-cyclohexenoesculetin-β-D-galactopyranoside.

27. A process according to claim 20 in which the esculetin compound is 3,4-cyclohexenoesculetin-β-D-galactopyranoside.

28. A process for detecting the presence of Samonella in a mixed sample suspected of containing Salmonella species including the steps of:
cutluring the mixed sample in the presence of a chromogenic α-galactosidase substrate to produce a culture product, and optically analyzing the culture product to detect the enzymic reaction product of the chromogenic α-galactosidase substrate, whereby a positive result is used as an indicator of the presence of Salmonella growth.

29. Process according to claim 28 in which the substrate is an indoxyl compound.

30. A process according to claim 29 in which the substrate is 5-bromo-4-chloro-3-indoxyl-α-D-galactopyranoside.

31. A process according to claim 30 in which the esculetin compound has the general formula I

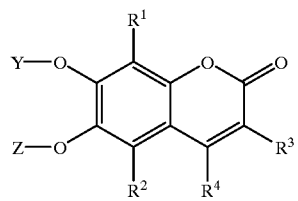

(I)

wherein each of $R^1$ and $R^2$ is independently selected from the group consisting of hydrogen, halogen atoms hydroxyl, $(C_{1-6})$alkyl and benzyl groups;

$R^3$ is selected from the group consisting of acyl groups of the general formula —COR, in which R is selected from the group consisting of $(C_1-C_8)$ alkyl, $(C_6$ and $C_{10})$aryl $(C_1-C_8)$ alkyl and $(C_5-C_8)$ cycloalkyl groups, $R^4$ is selected from the group consisting of hydrogen atoms, $(C_1-C_8)$ alkyl, $(C_6$ and $C_{10})$ aryl $(C_1-C_8)$ alkyl groups, optionally modified carboxyl-bearing group of the general formula —$CH_2(CH_2)_n COX$, where n is a number from 0 to 3 and X represents a hydroxyl group or another hydrophilic group provided that $R^3$ and $R^4$ between them contain at least three carbon atoms;

or $R^3$ and $R^4$ together with the carbon atoms to which they are attached form a $(C_5-C_8)$ cycloalkene ring; and one of Y and Z represents an enzymatically cleavable group and the other of Y and Z represents a hydrogen atom;

or a suitable salt or hydrate thereof.

32. A composition for use in the culturing of bacteria which comprises in admixture a first chromogenic enzyme substrate for β-galactosidase and a second chromogenic enzyme substrate, the substrates being such that the enzymic reaction products of the two enzymes are different compounds and wherein the second substrate is a substrate for α-galactosidase.

33. A composition according to claim 32 in which one of the substrates is an indoxyl compound.

34. A composition according to claim 33 in which the indoxyl compound is a 5-bromo-4-chloro-3-indolyl compound.

35. A composition according to claim 33 in which the other of the substrates is an esculetin compound.

36. A composition according to claim 35 in which the esculetin compound is a 3,4-cyclohexenoesculetin compound.

37. A composition according to claim 32 in which one of the substrates is an esculetin compound.

38. A composition according to claim 37 in which the esculetin compound has the general formula I

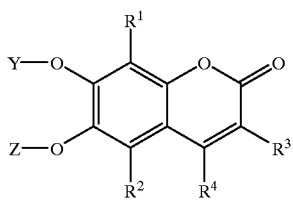

(I)

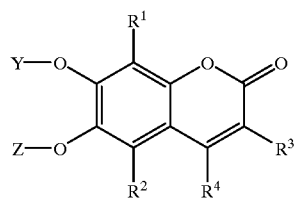

(I)

wherein
  each of $R^1$ and $R^2$ is independently selected from the group consisting of hydrogen, halogen atoms hydroxyl, $(C_{1-6})$alkyl and benzyl groups;
  $R^3$ is selected from the group consisting of acyl groups of the general formula —COR, in which R is selected from the group consisting of $(C_1-C_8)$ alkyl, $(C_6$ and $C_{10})$aryl $(C_1-C_8)$ alkyl and $(C_5-C_8)$ cycloalkyl groups,
  $R^4$ is selected from the group consisting of hydrogen atoms, $(C_1-C_8)$ alkyl, $(C_6$ and $C_{10})$ aryl $(C_1-C_8)$ alkyl groups, optionally modified carboxyl-bearing group of the general formula —$CH_2(CH_2)_n COX$, where n is a number from 0 to 3 and X represents a hydroxyl group or another hydrophilic group
  provided that $R^3$ and $R^4$ between them contain at least three carbon atoms;
  or $R^3$ and $R^4$ together with the carbon atoms to which they are attached form a $(C_5-C_8)$ cycloalkene ring; and
  one of Y and Z represents an enzymatically cleavable group and the other of Y and Z represents a hydrogen atom;
  or a suitable salt or hydrate thereof.

39. A composition according to claim 38 in which $R^3$ and $R^4$, together with the carbon atoms to which they are attached form a $C_{5-8}$ cycloalkene ring.

40. A composition according to claim 37 in which the esculetin compound is a 3,4-cyclohexenoesculetin compound.

41. A composition according to claim 32 which contains one or more nutrients for bacterial growth and a support substance.

42. A composition according to claim 41 in a dry hydratable form.

43. A composition according to claim 32 which contains an inhibitor of enterobacterial growth selected from the group consisting of brilliant green agar, agar containing bile salts, bismuth sulphite agar, agar containing desoxycholate salts, Hektoen enteric agar and Salmonella/Shigella agar.

44. A composition according to claim 32 which contains a promoter of β-galactosidase.

45. A composition according to claim 44 in which the promoter of β-galactosidase is selected from lactose, isopropyl-β-D-thiogalactopyranoside and mixtures thereof.

46. A composition for use in the culturing of bacteria comprising in admixture a first enzyme substrate which is an indoxyl compound and a second enzyme substrate, and wherein the second enzyme substrate is an esculetin compound.

47. A composition according to claim 46 in which the esculetin compound has the general formula I wherein
  each of $R^1$ and $R^2$ is independently selected from the group consisting of hydrogen, halogen atoms hydroxyl, $(C_{1-6})$alkyl and benzyl groups;
  $R^3$ is selected from the group consisting of acyl groups of the general formula —COR, in which R is selected from the group consisting of $(C_1-C_8)$ alkyl, $(C_6$ and $C_{10})$aryl $(C_1-C_8)$ alkyl and $(C_5-C_8)$ cycloalkyl groups,
  $R^4$ is selected from the group consisting of hydrogen atoms, $(C_1-C_8)$ alkyl, $(C_6$ and $C_{10})$ aryl $(C_1-C_8)$ alkyl groups, optionally modified carboxyl-bearing group of the general formula —$CH_2(CH_2)_n COX$, where n is a number from 0 to 3 and X represents a hydroxyl group or another hydrophilic group
  provided that $R^3$ and $R^4$ between them contain at least three carbon atoms;
  or $R^3$ and $R^4$ together with the carbon atoms to which they are attached form a $(C_5-C_8)$ cycloalkene ring; and
  one of Y and Z represents an enzymatically cleavable group and the other of Y and Z represents a hydrogen atom;
  or a suitable salt or hydrate thereof.

48. A composition according to claim 47 in which $R^3$ and $R^4$, together with the carbon atoms to which they are attached, form a cyclohexene ring.

49. A composition according to claim 46 which contains one or more nutrients for bacterial growth and a gelling substance.

50. A composition according to claim 49 in which the gelling substance is agar.

51. A composition according to claim 50 which contains a promoter of β-galactosidase.

52. A composition according to claim 51 in which the promoter of β-galactosidase is selected from the group consisting of lactose, isopropyl-β-D-thiogalactopyranoside and mixtures thereof.

53. A composition for use in the culturing of bacteria comprising agar, 5-bromo-4-chloro-3-indolyl-α-D-galactopyranoside and 3,4-cyclohexenoesculetin-β-D-galactopyranoside.

54. A composition according to claim 53 comprising an inhibitor of enterobacterial growth selected from the group consisting of brilliant green agar, agar containing bile salts, bismuth sulphite agar, agar containing desoxycholate salts, Hektoen agar and Salmonella/Shigella agar.

55. A composition according to claim 54 containing a promoter of β-galactosidase.

56. A composition according to claim 55 in which said promoter is selected from the group consisting of lactose, isopropyl-β-D-thiogalactopyranoside and mixtures thereof.

57. A composition according to claim 53 containing a promoter of β-galactosidase.

* * * * *